United States Patent
DiFoggio et al.

(10) Patent No.: US 8,379,207 B2
(45) Date of Patent: Feb. 19, 2013

(54) METHOD AND APPARATUS FOR ESTIMATING A FLUID PROPERTY

(75) Inventors: Rocco DiFoggio, Houston, TX (US); D. Duncan Blue, III, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 483 days.

(21) Appl. No.: 12/252,064

(22) Filed: Oct. 15, 2008

(65) Prior Publication Data

US 2010/0091288 A1 Apr. 15, 2010

(51) Int. Cl.
*G01N 21/00* (2006.01)
(52) U.S. Cl. .................. 356/437; 356/445; 356/448
(58) Field of Classification Search .................. 356/437, 356/445–448
See application file for complete search history.

(56) References Cited

U.S. PATENT DOCUMENTS

| | | | |
|---|---|---|---|
| 4,092,232 A | 5/1978 | Zetter | |
| 4,124,475 A | 11/1978 | Zetter et al. | |
| 4,154,659 A | 5/1979 | Zetter | |
| 4,157,283 A | 6/1979 | Zetter | |
| 4,994,671 A * | 2/1991 | Safinya et al. | 250/255 |
| 5,859,430 A * | 1/1999 | Mullins et al. | 250/255 |
| 5,898,517 A * | 4/1999 | Weis | 356/5.09 |
| 5,926,269 A | 7/1999 | Von Der Eltz et al. | |
| 6,223,822 B1 | 5/2001 | Jones | |
| 6,328,932 B1 | 12/2001 | Carter et al. | |
| 6,627,873 B2 * | 9/2003 | Tchakarov et al. | 250/256 |
| 6,939,717 B2 | 9/2005 | Jiang et al. | |
| 6,947,138 B2 | 9/2005 | Arno | |
| 6,995,899 B2 * | 2/2006 | Aronstam | 359/333 |
| 7,025,138 B2 | 4/2006 | Kurkjian et al. | |
| 7,671,983 B2 * | 3/2010 | Shammai et al. | 356/301 |
| 8,068,226 B2 * | 11/2011 | Csutak | 356/432 |
| 2004/0159149 A1 * | 8/2004 | Williams et al. | 73/152.23 |
| 2005/0205256 A1 * | 9/2005 | DiFoggio | 166/250.16 |
| 2007/0068242 A1 * | 3/2007 | DiFoggio | 73/152.55 |

OTHER PUBLICATIONS

Adcock, Ray N., Determination of H2S and Total Sulfur in Natural Gas, pp. 1-3, year 2005.
Graedel, T.E., et al., The Interaction of Hydrogen Sulfide with Lead- and Barium-Cadmium-Zinc-Stabilized Poly(vinyl Chloride), Journal of Applied Polymer Science, 1979, pp. 1769-1779, vol. 23, John Wiley & Sons, Inc.
Hadden, David M., A System for Continuous On-Site Measurement of Sulfides in Water-Base Drilling Muds, Society of Petroleum Engineers of AIME, 1977, pp. 81-92, American Institute of Mining, Metallurgical, and Petroleum Engineers, Inc.
Analyze It for Integrated Solutions: ABB: your partner in process analytics, 2004, pp. 1-12, ABB Inc.
International Search Report and Written Opinion, Mailed May 28, 2010, International Appln. No. PCT/US2009/060753, Written Opinion 4 Pages, International Search Report 7 Pages.

* cited by examiner

*Primary Examiner* — Tarifur Chowdhury
*Assistant Examiner* — Isiaka Akanbi
(74) *Attorney, Agent, or Firm* — Cantor Colburn LLP

(57) ABSTRACT

Apparatus and method for estimating a fluid property include an optic member having a material within the optic member responsive to the fluid property. A detector is operably associated with the optic member that detects a change in the material, the change being indicative of the fluid property.

20 Claims, 3 Drawing Sheets

METHOD AND APPARATUS FOR ESTIMATING A FLUID PROPERTY

BACKGROUND

1. Technical Field

The present disclosure generally relates to well bore tools and in particular to apparatus and methods for detecting a substance in a downhole fluid.

2. Background Information

Drilling tools and wireline tools are used to reach and evaluate subterranean formations that produce oil and gas. These tools often incorporate various sensors, instruments and control devices in order to carry out any number of downhole operations. The operations may include formation testing, fluid analysis, and tool monitoring and control.

Information about the subterranean formations traversed by the borehole may be obtained by any number of techniques. Techniques used to obtain formation information include obtaining one or more downhole fluid samples produced from the subterranean formations. Downhole fluids, as used herein include any one or any combination of drilling fluids, return fluids, connate formation fluids, and formation fluids that may be contaminated by materials and fluids such as mud filtrates, drilling fluids and return fluids. Downhole fluid samples are often retrieved from the borehole and tested in a rig-site or remote laboratory to determine properties of the fluid samples, which properties are used to estimate formation properties. Modern fluid sampling also includes various downhole tests to estimate fluid properties while the fluid sample is downhole.

Some formations produce hazardous fluids, such as hydrogen sulfide and other gases that may damage tools, present safety hazards to surface personnel, and that may reduce the viability of the formation for producing useful hydrocarbons. Surface testing for these fluids requires bringing the fluid to the surface. For H2S gas measurement, unless one is careful in the selection of sample tank material, retrieval of a sample to the surface runs the risk of under-reporting the actual H2S levels. The reason is that H2S chemically reacts with many materials. The unreacted, remaining amount of H2S in the sample that is finally measured at the surface may be significantly less than the total amount of H2S that had been in the original sample so that the H2S concentration gets under reported. That is another reason that an in-situ measurement is preferable. However, an in-situ measurement of the chemical composition of these fluids presents unique problems due to the rigorous downhole environment.

The environment in a well presents many challenges to maintain the tools used at depth due to vibration, harsh chemicals and temperature. Temperature in downhole tool applications presents a unique problem to these tools. High downhole temperatures may reach as high as 392° F. (200° C.) or more making it difficult to operate sensitive electronic components in the environment. Space in a downhole carrier is usually limited to a few inches in diameter. Cooling systems typically utilize large amounts of power and take up valuable space in the tool carrier and add an additional failure point in the system.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

Disclosed is an apparatus for estimating a fluid property. The apparatus may include an optic member having a material within the optic member that is responsive to the fluid property. A detector may be operably associated with the optic member that detects a change in the material, the change being indicative of the fluid property.

In another aspect, a method for estimating a fluid property includes introducing an optic member to a fluid. The optic member includes a material within the optic member that is responsive to the fluid property. The method may further include detecting a change in the material, the change being indicative of the fluid property.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DESCRIPTION OF EXEMPLARY EMBODIMENTS

The present disclosure uses terms, the meaning of which terms will aid in providing an understanding of the discussion herein. As used herein, high temperature refers to a range of temperatures typically experienced in oil production well boreholes. For the purposes of the present disclosure, high temperature and downhole temperature include a range of temperatures from about 100° C. to about 200° C. (about 212° F. to about 392° F.). In recent years, as wells have gotten deeper, a few wells now exceed 200° C. One or more embodiments disclosed herein may use the term carrier. The term "carrier" as used herein means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other carrier examples include casing pipes, wirelines, wireline sondes, slickline sondes, drop shots, downhole subs, bottom hole assemblies (BHA's), drill string inserts, modules, internal housings and substrate portions thereof.

Figure 1:
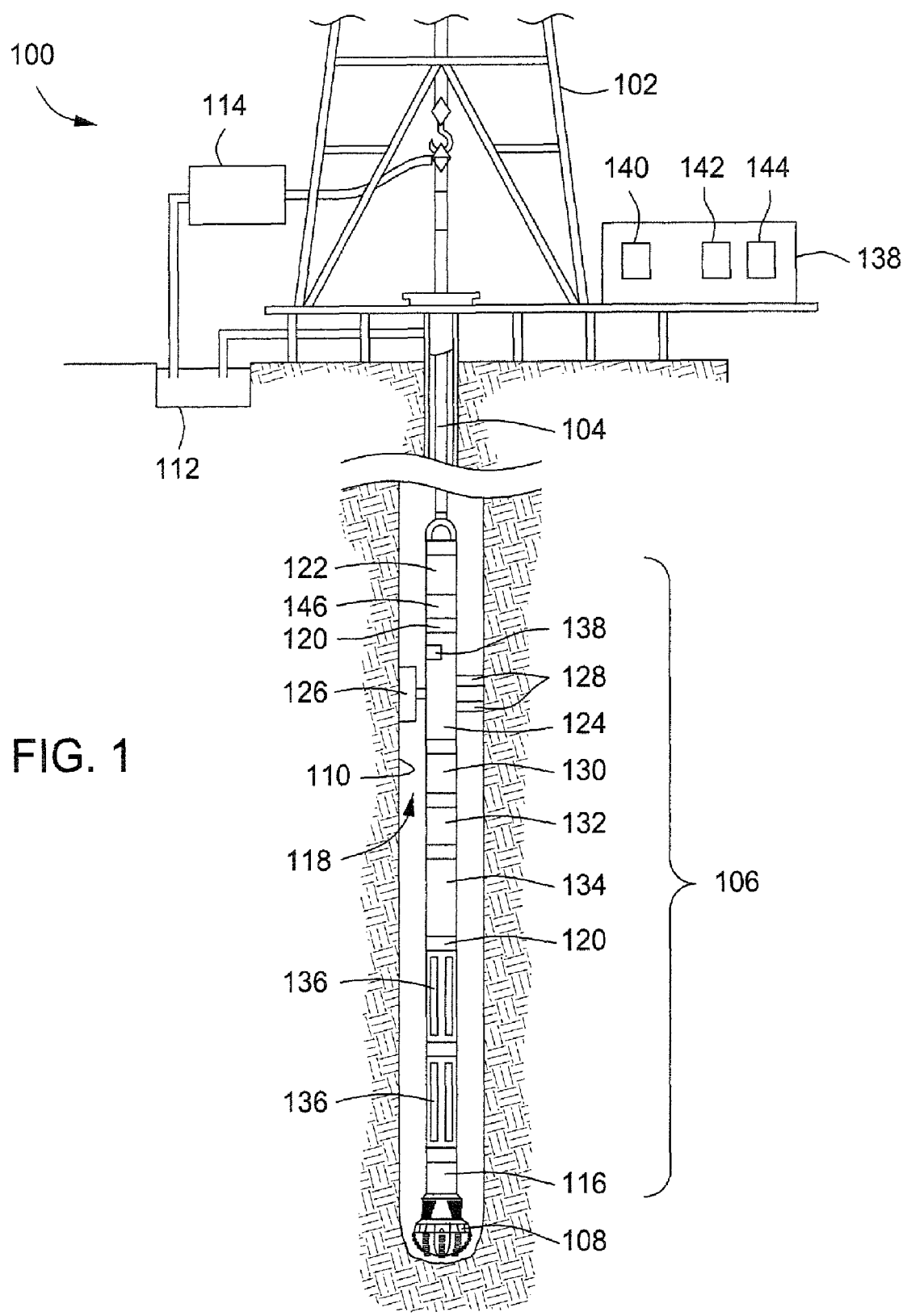
FIG. 1 schematically illustrates a non-limiting example of a drilling system in a measurement-while-drilling ("MWD") arrangement according to several non-limiting embodiments of the disclosure.

FIG. 1 schematically illustrates a non-limiting example of a drilling system 100 in a measurement-while-drilling ("MWD") arrangement according to several non-limiting embodiments of the disclosure. A derrick 102 supports a drill string 104 operating in this example as a carrier, which may be a coiled tube or drill pipe. The drill string 104 may carry a bottom hole assembly ("BHA") referred to as a downhole sub 106 and a drill bit 108 at a distal end of the drill string 104 for drilling a borehole 110 through earth formations.

Drilling operations according to several embodiments may include pumping drilling fluid or "mud" from a mud pit 112, and using a circulation system 114, circulating the mud through an inner bore of the drill string 104. The mud exits the drill string 104 at the drill bit 108 and returns to the surface through an annular space between the drill string 104 and inner wall of the borehole 110. The drilling fluid is designed to provide a hydrostatic pressure that is greater than the formation pressure to avoid blowouts. The pressurized drilling fluid may further be used to drive a drilling motor 116 and may be used to provide lubrication to various elements of the drill string 104.

In the non-limiting embodiment of FIG. 1, the downhole sub 106 includes a formation evaluation tool 118. The formation evaluation tool 118 may include an assembly of several tool segments that are joined end-to-end by threaded sleeves or mutual compression unions 120. An assembly of tool segments suitable for the present disclosure may include a power unit 122 that may include one or more of a hydraulic power unit, an electrical power unit and an electromechanical power unit. In the example shown, a formation sample tool 124 may be coupled to the formation evaluation tool 118 below the power unit 122.

The exemplary formation sample tool 124 shown comprises an extendable probe 126 that may be opposed by bore wall feet 128. The extendable probe 126, the opposing feet 128, or both may be hydraulically and/or electro-mechanically extendable to firmly engage the well borehole wall. The formation sample tool 124 may be configured for extracting a formation core sample, a formation fluid sample, formation images, nuclear information, electromagnetic information, and/or downhole information, such as pressure, temperature, location, movement, and other information. In several non-limiting embodiments, other formation sample tools not shown may be included in addition to the formation sample tool 124 without departing from the scope of the disclosure.

Continuing now with FIG. 1, several non-limiting embodiments may be configured with the formation sample tool 124 operable as a downhole fluid sampling tool. In these embodiments, a large displacement volume motor/pump unit 130 may be provided below the formation sample tool 124 for line purging. A similar motor/pump unit 132 having a smaller displacement volume may be included in the tool in a suitable location, such as below the large volume pump, for quantitatively monitoring fluid received by the downhole evaluation tool 118 via the formation sample tool 124. As noted above, the formation sample tool 124 may be configured for any number of formation sampling operations. Construction and operational details of a suitable non-limiting fluid sample tool 124 for extracting fluids are more described by U.S. Pat. No. 5,303,775, the specification of which is incorporated herein by reference.

The downhole evaluation tool 118 may include a downhole evaluation system 134 for evaluating several aspects of the downhole sub 106, of the drilling system 100, of the downhole fluid in and/or around the downhole sub 106, formation samples received by the downhole sub 106, and of the surrounding formation.

One or more formation sample containers 136 may be included for retaining formation samples received by the downhole sub 106. In several examples, the formation sample containers 136 may be individually or collectively detachable from the downhole evaluation tool 118.

A downhole transceiver 146 may be coupled to the downhole sub 106 for bidirectional communication with a surface transceiver 140. The surface transceiver 140 communicates received information to a controller 138 that includes a memory 142 for storing information and a processor 144 for processing the information. The memory 142 may also have stored thereon programmed instructions that when executed by the processor 144 carry out one or more operations and methods that will become apparent in view of the discussion to follow. The memory 142 and processor 144 may be located downhole on the downhole sub 106 in several non-limiting embodiments.

The system 100 shown in FIG. 1 is only an example of how various tools may be carried into a well borehole using the downhole sub 106. Tools according to the present disclosure may further include direct measurement tools for evaluating fluid characteristics such as content and concentrations. In one or more embodiments, the downhole sub 106 may be used to carry a downhole gas detector for evaluating fluids in-situ. The following discussion and associated figures will present several exemplary downhole gas detectors according to the disclosure.

Figure 2:
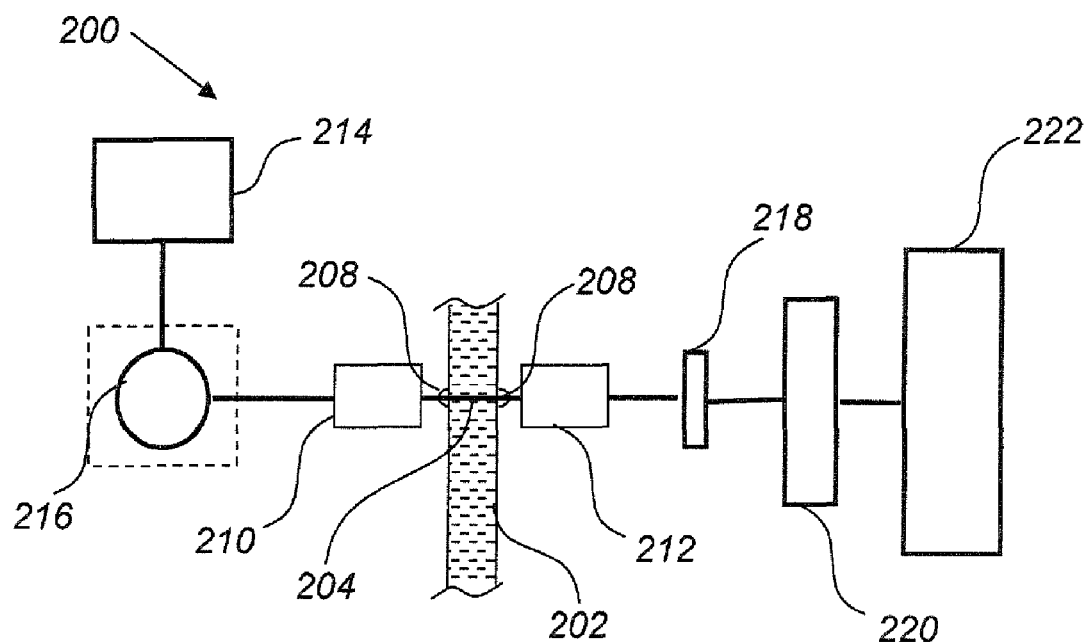
FIG. 2 illustrates non-limiting example of a gas detection tool according to one or more embodiments of the disclosure.

FIG. 2 illustrates a non-limiting example of a downhole fluid test tool 200 that may be incorporated into the downhole sub 106 as part of the downhole evaluation system 134 described above and shown in FIG. 1. As used herein, downhole fluid means any fluid that is carried to, carried in, encountered in, or carried from a downhole environment. A downhole fluid may include drilling fluid, return fluid, formation fluid or any combination thereof. The downhole fluid test tool 200 includes a fluid cell 202. In the non-limiting embodiment of FIG. 2, an optic member 204 is shown immersed in the fluid 206. The fluid cell 202 may include a septum 208 as an interface with the fluid cell 202 and the optic member 204. The optic member may be introduced to the fluid via a feeder 210, and a receiver 212 may be disposed to receive the optic member 204.

One or more embodiments may further include a controller 214 coupled to an electromagnetic energy light source 216 and the electromagnetic energy source 216 may be coupled to the feeder 210 as shown, to the optic member 204, or to both. In one or more embodiments, the receiver 212 may be coupled to a photo detector 218. The photodetector 218, depending on the detector output signal characteristics, may be connected to an analog-to-digital converter (ADC) 220 and the ADC 220 may be connected to a controller 222. In one or more embodiments, the light source controller 214 and the controller 222 connected to the ADC 220 or photodetector 218 may be implemented as a single controller without departing from the scope of the disclosure.

The controller or controllers 214, 222 may be implemented as downhole controllers or as surface controllers substantially as described above and shown in FIG. 1 as surface controller 138. The controller 214, 222 may include a memory 142 as shown in FIG. 1 containing programs for carrying out instructions for methods to be described in more detail below.

The electromagnetic energy source 216 may be any suitable source for generating one or more wavelengths of electromagnetic energy. The generated energy may include broadband, narrow band, a single wavelength, or combinations thereof. In one or more embodiments, the electromagnetic energy source may include a broadband source such as a tungsten bulb that produces substantially white light. The filament temperature of a tungsten bulb is approximately 2700 C. so its operation is substantially unaffected at wellbore temperatures of 200 C. In one or more embodiments, the electromagnetic energy source may include an LED, a laser diode, or a combination thereof. The laser diodes and LEDs, when used may be provided cooling to avoid dimming at elevated temperatures. In one or more embodiments, the electromagnetic energy source may include a plurality of sources arranged in an array.

The feeder 210 may include any suitable mechanism for introducing the optical member 204 to the fluid 206. In one or more embodiments, the feeder 210 may include a probe with the optical member 204 being disposed on the probe. The optical member, such as a polymer fiber optic, being insertable into the fluid cell 202 through a hole in an elastomeric, self-sealing septum 208. Those skilled in the art with the benefit of the present disclosure will appreciate that the fluid need not be in a tool-carried fluid cell. In one or more embodiments, the fluid may be in the wellbore annulus and the optical member may be extended from the tool and into the annulus fluid. In one or more embodiments, an optical member 204 may be inserted into a formation. It should also be recognized that the feeder 210 and optical member 204 need not penetrate through a fluid cell 202 as depicted in the non-limiting example of FIG. 2. The optical member 204 may be arranged as a loop with the photodetector 218, ADC 220 and controller 222 being arranged co-located with the feeder 210. The feeder 210, the receiver 212, or each of the feeder and receiver may include a mechanism for disposing of used optical members and for dispensing new optical members for multiple test capability.

Figure 3:
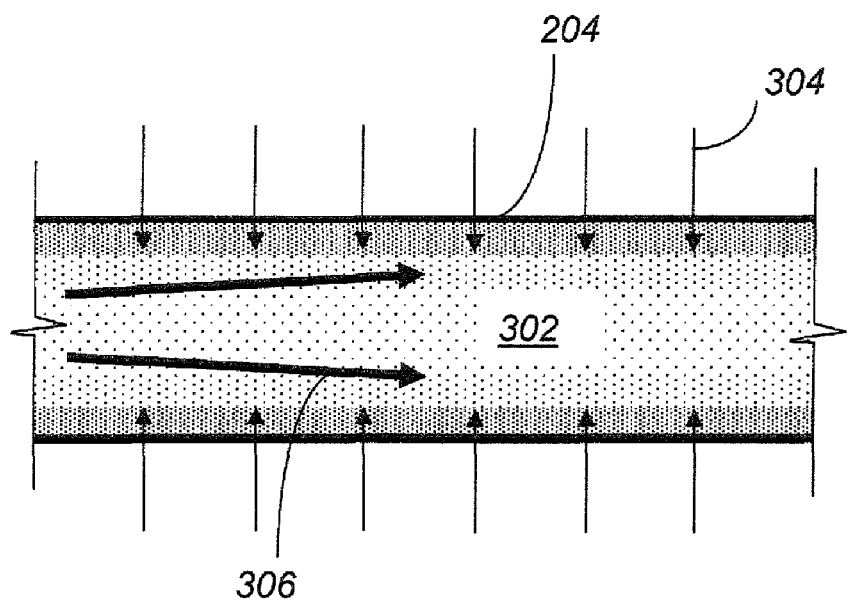
FIG. 3 illustrates a filled fiber detector according to one or more embodiments of the disclosure.

Referring now to FIGS. 2 and 3, the optical member 204 in several embodiments may include a fiber 300 having a calorimetric filler 302 disposed within the fiber. In one or more embodiments, the fiber 300 may be manufactured using a high-refractive-index, high-temperature polymer such as the transparent sulfone polymers, such as a polysulfone, a polyethersulfone, or a combination thereof. Each of these materials may be used in high-temperatures as may be experienced in the downhole environment. For example, polysulfones are capable of use in temperatures at least up to 174 C. and polyphenylsulfones are usable to about 204 C. In one or more embodiments, the fiber 300 may be a clear The calorimetric filler 302 may be any filler responsive to interaction with a gas 304 penetrating the fiber 300. In one or more embodiments, the filler may include a small amount (1%-2% by weight) of a compound that contains lead, iron, or another substance that changes color upon exposure to a selected gas 304 such as H2S. In one or more embodiments, lead sulfate, which melts at the very high temperature of 1170 C., may be used as the filler 302. In other embodiments, an iron compound may be used as the calorimetric filler 302. For example, hydrogen sulfide reacts with ferric oxide, Fe2O3, which is rust colored, to form ferrous sulfide, FeS2, which is black. Elemental iron particles might also be used as the colorimetric filler. In other non-limiting examples, high temperature organic compounds that change color upon exposure to a selected gas such as H2S may be used as the filler 302. Similarly, for SO2 detection, the color-changing filler could be an alkali vanadate such as sodium vanadate, which doesn't melt until 858 C or potassium dichromate, which doesn't melt until 398 C. Similarly, other gases could be detected using other color-changing fillers.

Figure 4:
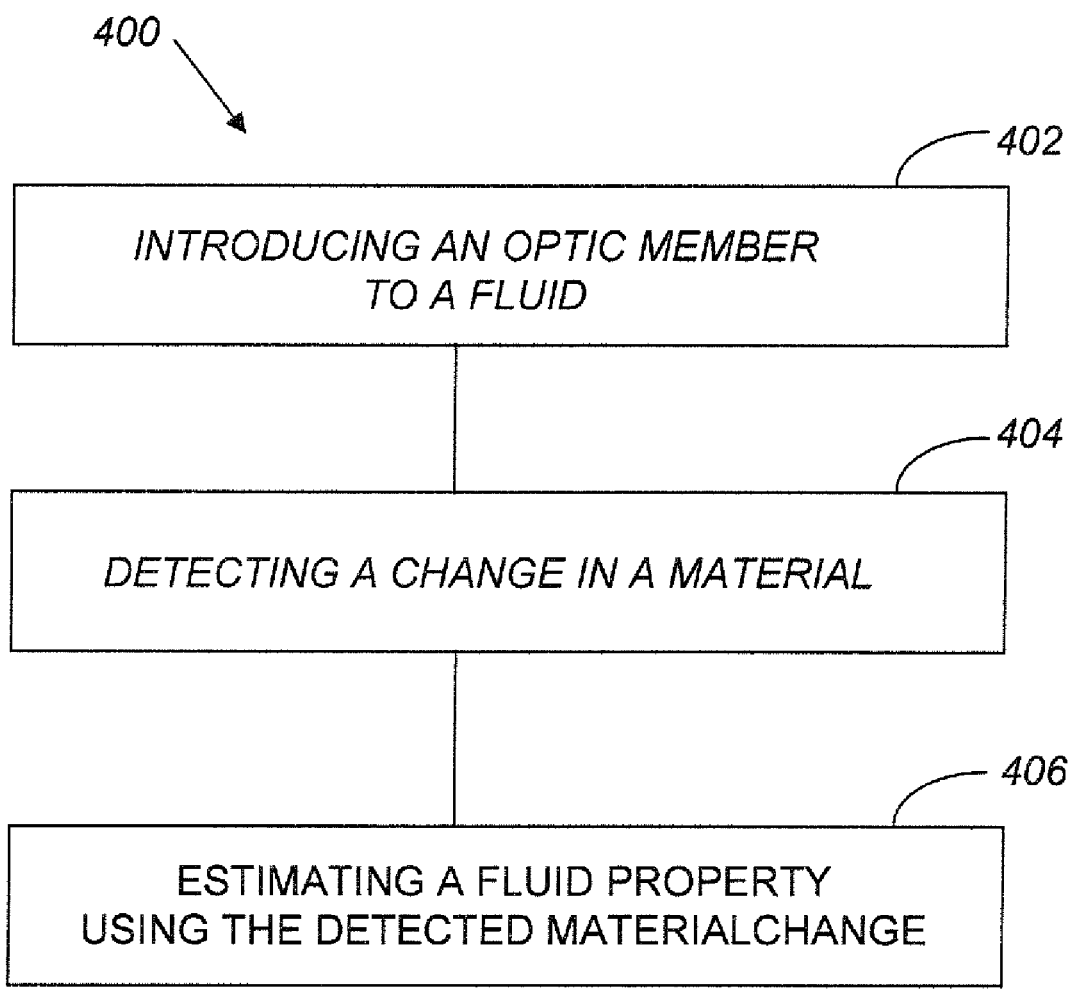
FIG. 4 illustrates a non-limiting method according to one or more embodiments of the disclosure.

Operational examples may now be described in view of the several embodiments described above and shown in FIGS. 1-3. Referring to FIG. 4, a method 400 for estimating a fluid property may include introducing an optic member to a fluid 402. A material change may then be detected 204, and the fluid property may be estimated 406 using the detected material change. In one or more embodiments, the estimated property may be quantitative, qualitative, or a combination thereof.

In one or more embodiments, the optical member 204 may be implemented as a simple H2S sensor that can be directly immersed into a high-temperature, high-pressure fluid downhole and produce to produce real-time H2S concentration measurements. An advantage is that the H2S diffuses out of the downhole fluid into a filled polymer thus accomplishing both a separation step through diffusion into the bulk polymer and the detection step through attenuation of light 306 transmitted because of discoloration of the filler as shown in FIG. 3. Dissolved gases 304, such as H2S, diffuse into the polymer, react with the filler, and discolor or darken from the outer perimeter of the member 204 toward the interior as shown in FIG. 3. The rate of discoloring or darkening of the polymer would be indicative of the H2S concentration in the downhole fluid.

The polymer may be selected such that the polymer can withstand borehole temperatures up to about 200 C. without melting and should be optically transparent. Selection should also take into consideration that the polymer should have a refractive index that is greater than the refractive index of crude oil (typical range of 1.40-1.55) and the refractive index of brine (typical range of 1.30-1.38). A high-refractive-index, high-temperature, transparent polymer such as the sulfone polymers could be used. For example, Udel® is a polysulfone usable to 174 C., Radel® A and Radel® R are polyethersulfones usable to 204 C. These exemplary polysulfones are available from Solvay Advanced Polymers 4500 McGinnis Ferry Road, Alpharetta, Ga. 30005-3914 USA. In one or more embodiments, the sulfone polymer may be loaded with a small amount of H2S-indicating filler and drawn into a fiber. A light source 216 may be attached to one end of the fiber and a light detector 218 may be attached to the other end of the fiber. The middle section of fiber 204 may be immersed in the downhole fluid with appropriate fluid-tight connectors 208 at both ends. As noted above, one example of a suitable connector may include a self-sealing septum device. Light will propagate along the optic member 204 when a higher index of refraction (RI) exists within the fiber than in the medium surrounding the fiber. This condition is met by the exemplary sulfones mentioned above where Udel® RI=1.650 at 486 nm, Radel® A RI=1.671 at 486 nm, or Radel® R RI=1.696 at 486 nm is immersed in crude oil, brine, or natural gas because the RI of crude oil is generally between 1.40 and 1.55, the RI of brine is generally between 1.30 and 1.38, and the RI of natural gas is generally between 1.1 and 1.3 depending on pressure and temperature. By observing rate of change of the attenuation of light transmitted at one or more wavelengths through the fiber and accounting for the temperature and/or pressure dependence of the H2S diffusion rate into the polymer, we can estimate the H2S concentration of the downhole fluid.

The color-changing filler selected should be stable and it should not decompose at borehole temperatures. In one or more embodiments, the selected filler provides a significant color change upon exposure to expected concentrations of the gas in the downhole fluids. Using a lead sulfate filler provides for a very high melting temperature of 1170 C. Alternatively, an iron compound might be used as the calorimetric filler. For example, hydrogen sulfide reacts with ferric oxide, Fe2O3, which is rust colored, to form ferrous sulfide, FeS2, which is black. Elemental iron particles might also be used as the colorimetric filler. In other embodiments a high temperature organic compounds that change color upon exposure to H2S may be used.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

Given the above disclosure of general concepts and specific embodiments, the scope of protection is defined by the claims appended hereto. The issued claims are not to be taken as limiting Applicant's right to claim disclosed, but not yet literally claimed subject matter by way of one or more further applications including those filed pursuant to the laws of the United States and/or international treaty.

What is claimed is:

1. An apparatus for estimating a fluid property comprising:
a downhole carrier;
an optic member disposed at the downhole carrier and configured to be exposed to downhole fluid;
a material disposed within the optic member in at least a radially central portion of the optic member, the material responsive to interaction with components of the downhole fluid that penetrate the optic member; and
a detector operably associated with the optic member that detects a change in the material, the change being indicative of the fluid property.

2. An apparatus according to claim 1, wherein the optic member comprises a polymer fiber including a polymer material configured to withstand temperatures in a downhole environment.

3. An apparatus according to claim 2, wherein the polymer fiber comprises one or more sulfone polymers.

4. An apparatus according to claim 2, wherein the polymer fiber comprises one or more of a polysulfone, a polyethersulfone, or a combination thereof.

5. An apparatus according to claim 2, wherein the polymer material has a refractive index greater than at least one of crude oil and brine.

6. An apparatus according to claim 1, wherein the material includes one or more of lead, iron, lead sulfate, an iron compound, ferric oxide, elemental iron particles, an organic compound, or combinations thereof.

7. An apparatus according to claim 1, wherein the fluid property includes the presence of a gas.

8. An apparatus according to claim 7, wherein the gas includes at least one of a sulfide and hydrogen sulfide.

9. An apparatus according to claim 1, further comprising at least one of a feeder that moves the optical member toward the fluid and a device for replacing the optical member after use.

10. A method for estimating a fluid property comprising:
disposing an optical member in a borehole via a downhole carrier;
introducing the optic member to a downhole fluid, the optic member including a material disposed within the optic member in at least a radially central portion of the optic member, the material responsive to interaction with components of the downhole fluid that penetrate the optic member; and
detecting a change in the material, the change being indicative of the fluid property.

11. A method according to claim 10, wherein the optic member comprises a polymer fiber including a polymer material configured to withstand temperatures in a downhole environment.

12. A method according to claim 11, wherein the polymer fiber comprises one or more of a polysulfone, a polyethersulfone, or a combination thereof.

13. A method according to claim 11, wherein the polymer material has a refractive index greater than at least one of crude oil and brine.

14. A method according to claim 10, wherein the polymer fiber comprises one or more sulfone polymers.

15. A method according to claim 10, wherein the material includes one or more of lead, iron, lead sulfate, an iron compound, ferric oxide, elemental iron particles, an organic compound, or combinations thereof.

16. A method according to claim 10, further comprising introducing electromagnetic energy to the optic member.

17. A method according to claim 16, wherein detecting a change in the material includes detecting an attenuation of the electromagnetic energy.

18. A method according to claim 10, further comprising replacing the optical member after use.

19. A method according to claim 10, wherein the fluid property includes the presence of at least one of a sulfide and hydrogen sulfide.

20. A method according to claim 10, wherein detecting a change in the material includes detecting a rate of change of the material from an outer perimeter of the optic member toward the radially central portion.

* * * * *